(12) United States Patent
Birdsley et al.

(10) Patent No.: US 6,355,564 B1
(45) Date of Patent: Mar. 12, 2002

(54) SELECTIVE BACK SIDE REACTIVE ION ETCH

(75) Inventors: Jeffrey D. Birdsley; Matthew Thayer, both of Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/384,080

(22) Filed: Aug. 26, 1999

(51) Int. Cl.[7] .................. H01L 21/66; H01L 21/302
(52) U.S. Cl. ................ 438/689; 438/14; 438/719
(58) Field of Search .................. 438/689, 719, 438/14, 17, 459, 5

(56) References Cited

U.S. PATENT DOCUMENTS

| | | | |
|---|---|---|---|
| 3,679,502 A | * 7/1972 | Hays | 156/17 |
| 3,997,381 A | * 12/1976 | Wanlass | 156/17 |
| 4,637,853 A | * 1/1987 | Bumble et al. | 156/345 |
| 5,086,011 A | 2/1992 | Shiota | 438/406 |
| 5,372,673 A | * 12/1994 | Stager et al. | 156/626 |
| 5,582,746 A | * 12/1996 | Barbee et al. | 216/86 |
| 5,658,418 A | * 8/1997 | Coronel et al. | 156/345 |
| 5,711,851 A | * 1/1998 | Blalock et al. | 156/643.1 |
| 5,935,874 A | * 8/1999 | Kennard | 438/710 |
| 5,972,725 A | * 10/1999 | Wollesen et al. | 438/14 |
| 6,084,257 A | * 7/2000 | Petersen et al. | 438/50 |
| 6,093,331 A | * 7/2000 | Wollesen | 216/2 |
| 6,103,009 A | * 8/2000 | Atoji | 438/459 |

OTHER PUBLICATIONS

Thong, J.T.L., Choi, W.K., Chong, C.W., *TMAH Etching of Silicon and the Interaction of Etching Parameters*, 1997, pp. 1–7.

Material Safety Data Sheet—Tetramethylammonium hydroxide, 25% (Aqueous solution) pp. 1–5, No date.

Malberti, P., Ciappa, M., Scacco, P., *A New Back–Etch for Silicon Devices*, 1997, pp. 257–261.

* cited by examiner

Primary Examiner—Michael Trinh

(57) ABSTRACT

According to an example embodiment, a semiconductor device having a back side and a circuit side opposite the back side is analyzed. The semiconductor device includes bulk silicon in the back side and also includes epitaxial silicon. An ion gas comprising $SF_6$ and $N_2$ is directed at a target region in the back side. Using the ion gas, the target region in the back side is selectively etched using reactive ion etching (RIE) and an exposed region is formed. The etching is selective to the bulk silicon. When the etching process encounters the epitaxial silicon, the etch rate slows and is used as an endpoint indicator of the selective etching process. Once the etching process is stopped, the circuitry is accessed via the exposed region.

18 Claims, 3 Drawing Sheets

SELECTIVE BACK SIDE REACTIVE ION ETCH

FIELD OF THE INVENTION

The present invention relates generally to semiconductor devices and their fabrication and, more particularly, to semiconductor devices and their manufacture involving reactive ion etching.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages. A by-product of such high-density and high functionality in semiconductor devices has been the demand for increased numbers of external electrical connections to be present on the exterior of the die and on the exterior of the semiconductor packages which receive the die, for connecting the packaged device to external systems, such as a printed circuit board.

To increase the number of pad sites available for a die, to reduce the electrical path to the pad sites, and to address other problems, various chip packaging techniques have been developed. One of these techniques is referred to as controlled collapse chip connection or "flip-chip" packaging. With packaging technology, bonding pads of the die include metal (solder) bumps. Electrical connection to the package is made when the die is "flipped" over and soldered to the package. Each bump connects to a corresponding package inner lead. The resulting packages are low profile and have low electrical resistance and a short electrical path. The output terminals of the package, which are sometimes ball-shaped conductive bump contacts, are typically disposed in a rectangular array. These packages are occasionally referred to as "Ball Grid Array" (BGA) packages. Alternatively, the output terminals of the package may be pins and such packages are commonly known as pin grid array (PGA) packages.

Once the die is attached to such a package the back side portion of the die remains exposed. The transistors and other circuitry are generally formed in a very thin epitaxially-grown silicon layer on a single crystal silicon wafer from which the die is singulated. The side of the die including the epitaxial layer containing the transistors and other circuitry is often referred to as the circuit side or front side of the die. The circuit side of the die is positioned very near the package and opposes the back side of the die. Between the back side and the circuit side of the die is bulk silicon.

The positioning of the circuit side near the package provides many of the advantages of the flip chip. However, in some instances orienting the die with the circuit side face down on a substrate is disadvantageous. Due to this orientation of the die, the transistors and circuitry near the circuit side are not directly accessible for analyzing, modification or other purposes. Therefore, access to the transistors and circuitry near the circuit side is from the back side of the chip.

For flip-chips and other dies requiring or benefiting from back side access, techniques have been developed to access the circuit even though the integrated circuit (IC) is buried under the bulk silicon. For example, near-infrared (nIR) microscopy is capable of imaging the circuit because silicon is relatively transparent in these wavelengths of the radiation. However, because of the absorption losses of nIR radiation in silicon, it is generally required to thin the die to less than 100 microns in order to view the circuit using nIR microscopy. For a die that is 725 microns thick, at least 625 microns of silicon is removed before nIR microscopy can be used.

Thinning the die for analysis of an IC requiring or benefiting from back side access is usually accomplished by first globally thinning, wherein the silicon is thinned across the entire die surface. The silicon is globally thinned to allow viewing of the active circuit from the back side of the die using nIR microscopy. Mechanical polishing and chemical-mechanical polishing are two example methods for global thinning. Using nIR microscopy, an area is identified for accessing a particular area of the circuit.

An example method for etching a semiconductor device is a form of dry etching called reactive ion etching (RIE). In a typical dry etch process, reactive species are first generated in a plasma. The species then diffuse to the substrate surface being etched, where they are adsorbed. A chemical reaction occurs, and a volatile by-product is formed. The by-product is then desorbed from the surface and diffused into the bulk of the gas. RIE is one such type of dry etching which is often used to selectively etch a substrate on which desired features of an integrated circuit have been defined using a process such as photo-lithography. In RIE, a process gas is introduced into a chamber. Plasma is generated in the chamber and used to create an etch gas from the process gas. The etch gas etches the substrate and creates volatile etch byproduct compounds which are evacuated from the chamber.

Near-infrared microscopy, however, generally requires that the surface through which an image is obtained is substantially flat and non-pitted. This requirement has made the use of RIE via the back side of semiconductor devices difficult or not feasible, since existing methods for RIE are often either too slow for efficient processing or result in surfaces that are substantially non-planar, pitted, and generally not conducive to nIR microscopy. For example, prior applications for RIE have been limited in substrate removal rate to about 0.4 micrometers per minute. Such removal rates are not acceptable for efficient processing. In addition, methods for back side RIE often require the time it takes the etch process to reach the endpoint be known in order to determine when to stop etching.

SUMMARY OF THE INVENTION

The present invention is exemplified in a number of implementations and applications, some of which are summarized below. According to an example embodiment, the present invention is directed to a method for analyzing a semiconductor device having a back side and a circuit side opposite the back side. The semiconductor device includes bulk silicon in the back side and also includes epitaxial silicon. An ion gas comprising $SF_6$ and $N_2$ is directed at a target region in the back side. Using the ion gas, the target region in the back side is selectively etched using reactive ion etching (RIE) and an exposed region is formed. The etching is selective to the bulk silicon. The epitaxial silicon is used as an endpoint indicator of the step of selectively etching, and the circuitry is accessed via the exposed region.

The above summary of the present invention is not intended to describe each illustrated embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
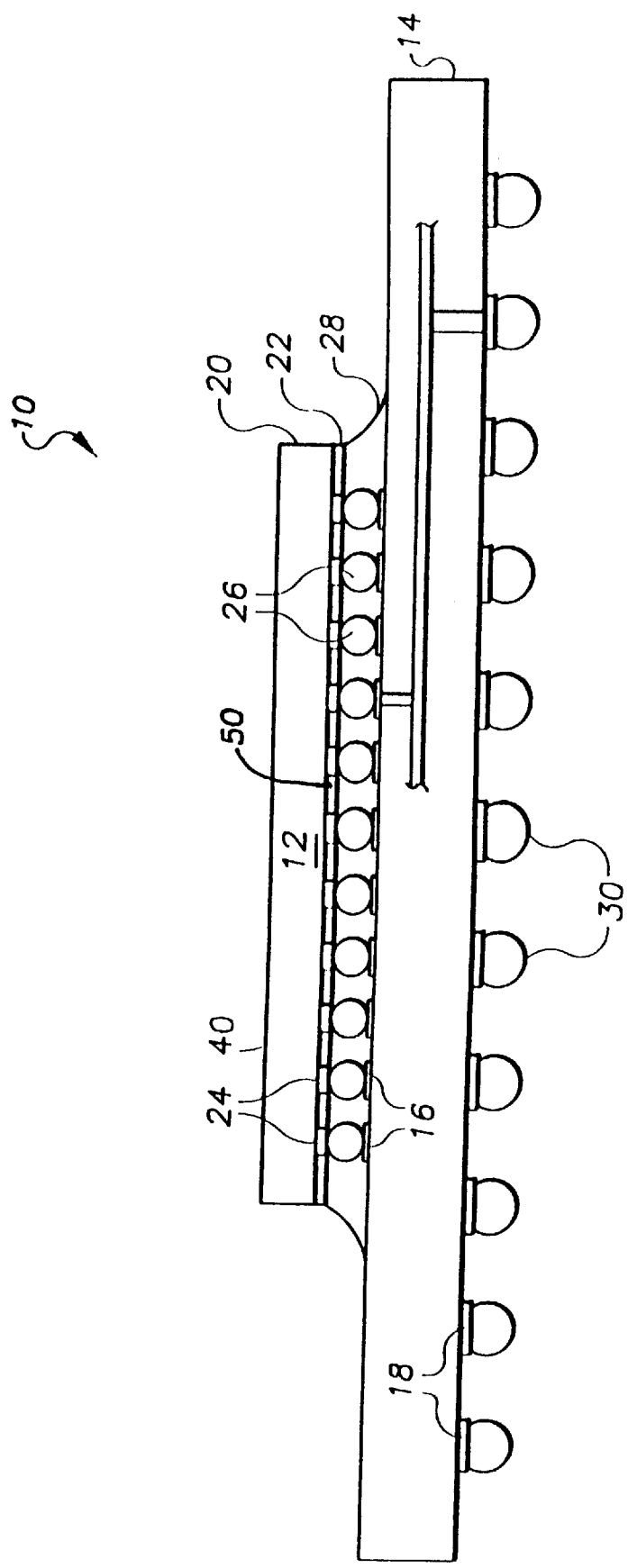
FIG. 1 is a flip-chip type die attached to a package substrate, for use in accordance with the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable to a variety of different types of semiconductor devices, and the invention has been found to be particularly suited for flip-chip and other devices requiring or benefiting from back side etching. While the present invention is not necessarily limited to such devices, various aspects of the invention may be appreciated through a discussion of various examples using this context.

In connection with the present invention, FIG. 1 shows a side view of an assembly 10 of one type of conventional flip chip type die 12 assembled to a package substrate 14. Flip chip die 12 has a circuit side 50 and a back side 40. The circuit side 50 includes a number of circuit devices formed near the circuit side in a portion of the die known as the epitaxial layer 22. The epitaxial layer 22 has a thickness in the range of 1 to 15 microns. The portion of the die shown above the epitaxial layer is known as the bulk layer 20. A plurality of solder bumps 26 are made on the circuit side 50 at pads 24. The solder bumps 26 are the inputs and outputs to the circuitry associated with the die 12. The flip chip type die 12 is attached to package substrate 14, such as a package for a flip chip via the solder bumps on the die 12. The package substrate 14 includes pads 16 which are arranged to correspond to the pattern of solder bumps on the die 12. The region between integrated circuit 12 and package substrate 14 is filled with an under-fill material 28 to encapsulate the solder bump connections and provide additional mechanical benefits. The pads 16 are coupled via circuitry to pads 18 on the package substrate. Solder bumps 30 are formed on the pads 18. The solder bumps 30 are the inputs and outputs to the circuitry associated with the package substrate 14. In another arrangement (not illustrated), the inputs and outputs to the circuitry associated with the package substrate 14 are implemented as pins rather than solder bumps.

Figure 2:
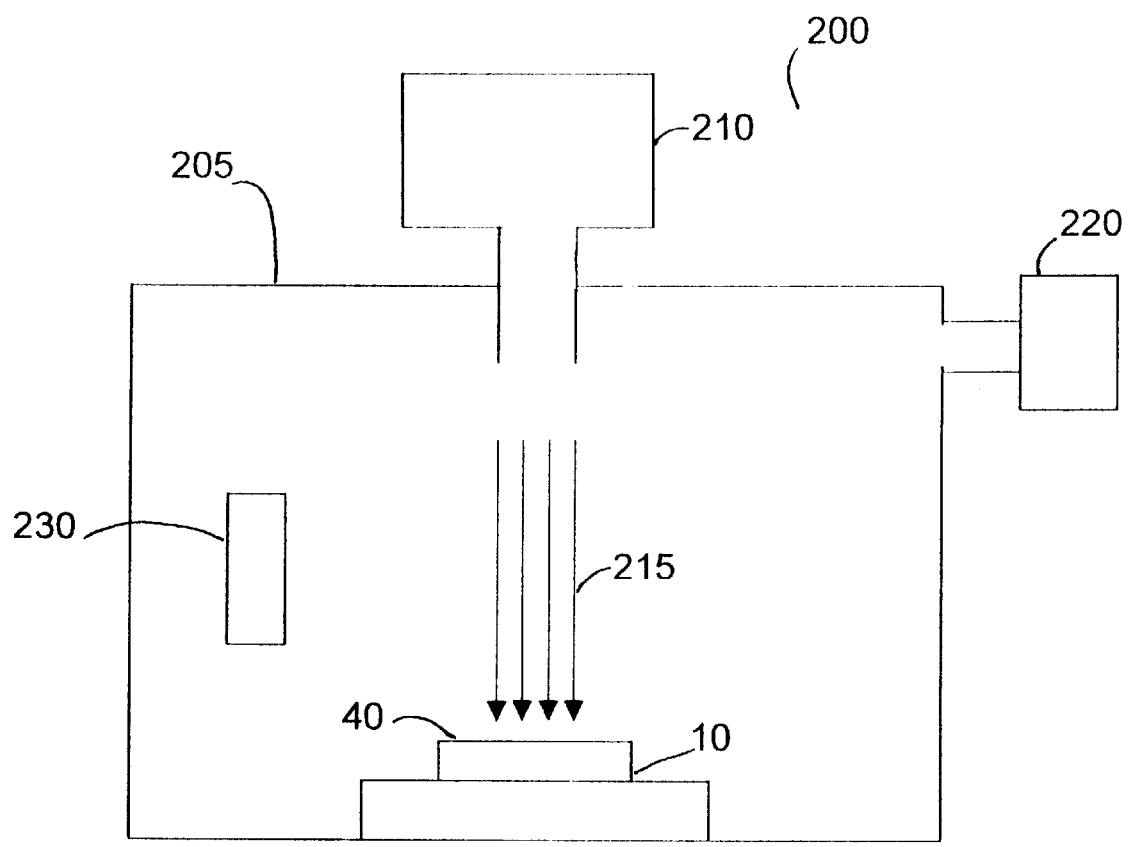
FIG. 2 shows a flip-chip die, such as shown in FIG. 1, undergoing back side RIE, according to another example embodiment of the present invention.

FIG. 2 shows a flip-chip type die 10 undergoing RIE in an apparatus 200, according to another example embodiment of the present invention. The die 10 is located in a processing chamber 205. A process gas supply 210 is used to supply $SF_6$ and $N_2$ gas to the chamber 205. A power supply 230 is used to generate plasma in the chamber, and creates an etch gas from the process gas. The etch gas etches the back side 40 of the die 10 and creates a byproduct, which is removed from the chamber by a pump 220. RIE equipment such as that included in the apparatus 200 is available from Plasma Therm of St. Petersburg, Fla. and Trion Technology of Tempe, Ariz.

In connection with the present invention, and according to an example embodiment, it has been discovered that the back-side of a semiconductor device can be etched without damaging the device and the endpoint of the etching process can be detected using a RIE process that uses $SF_6$ and $N_2$ as process supply gases for generating the etch gas via a plasma generator. In a more particular example embodiment, a semiconductor device is etched using an RIE process with a supply power of about 500 watts, a process ion gas supply of $SF_6$ at about 48 SCFM and $N_2$ at about 48 SCFM, and a chamber pressure of about 250 mtorr. The process is carried out in a chamber with the temperature being monitored or controlled by pausing the process to ensure that the die does not overheat. The semiconductor device includes bulk silicon in the back side and also includes epitaxial silicon, and the RIE process is selective to the bulk silicon. The bulk silicon is more highly doped than the epitaxial silicon. Nitrogen provides better etch uniformity and planarity, and less surface pitting across the device than traditional applications that use oxygen. Using this recipe, the back side of a semiconductor device can be etched at an acceptable etch-rate, such as a rate in a range including about four micrometers per minute. Furthermore, the etching process can be accomplished with out damaging the circuitry or substrate in the device, and the resulting surface is readily adaptable for imaging the device via the back side, such as using infrared microscopy.

The endpoint of the etch process is detected using the selectivity of the etch gas to the bulk silicon. Due to the selectivity, the bulk silicon is etched at a rate of about 10 to 20 times faster than the epitaxial silicon is etched. The epitaxial silicon is used as an endpoint indicator of the etching process. For example, the etch rate can be monitored and the etch process can be controlled responsive to the monitored etch rate reaching a threshold defined as a function of the semiconductor device and the etch process. The threshold can be defined to include a decrease in etch rate to reflect the difference between the etch rate of the bulk silicon and the epitaxial silicon. According to a more particular example embodiment of the present invention, a computer arrangement is adapted to monitor the etch process, determine the endpoint of the etch process, and stop the process in response to determining that the endpoint has been reached.

In addition, and according to another example embodiment of the present invention, the semiconductor device may be thinned using a combination of methods. For example, the semiconductor can be thinned to about 100 microns prior to using the RIE process. The device can then be thinned using RIE to locally or globally thin the remaining silicon. In another example, RIE is used to globally thin the device, and subsequently used to locally thin a device and to expose a target region.

In a more particular example embodiment of the present invention, substrate in the back side of the device is also sputtered, contributing to the etch process. The sputtering rate increases with increasing ion impingement on the surface.

Figure 3:
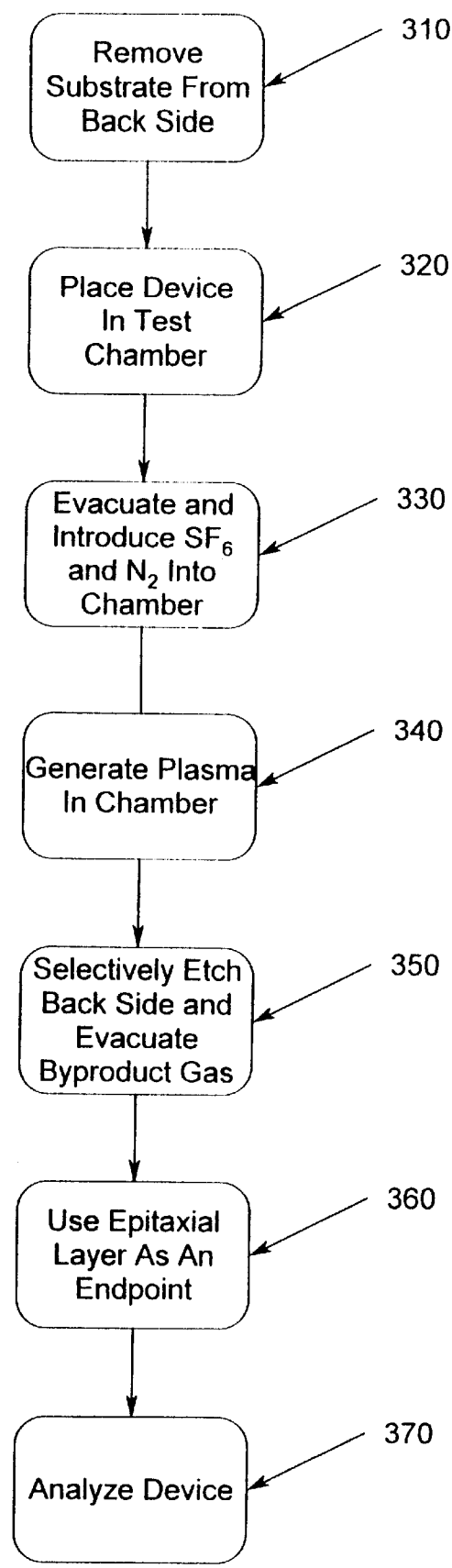
FIG. 3 is a flow diagram of a method for analyzing a semiconductor device, according to another example embodiment of the present invention.

FIG. 3 is a flow chart for a method of analyzing a semiconductor device, according to another example embodiment of the present invention. Substrate is removed from the back side of a semiconductor device at block 310. The device is then placed in a test chamber at block 320. The chamber is evacuated and $SF_6$ and $N_2$ are introduced into the chamber at block 330. An RF generator is used to generate plasma and form an etch gas in the chamber at block 340, and the back side is selectively etched at block 350. The etching step generates a byproduct gas, which is evacuated from the chamber, also at block 350. The epitaxial layer is used as an endpoint of the etching process at block 360. After the endpoint has been reached, the device is analyzed via the back side at block 370.

While the present invention has been described with reference to several particular example embodiments, those skilled in the art will recognize that many changes may be made thereto without departing from the spirit and scope of the present invention, which is set forth in the following claims.

What is claimed is:

1. A method for analyzing a semiconductor device having a back side and a circuit side opposite the back side, wherein the semiconductor device includes bulk silicon in the back side and also includes epitaxial silicon, the method comprising:

directing ion gas comprising $SF_6$, and $N_2$ at a target region in the back side;

using the ion gas, selectively etching the target region in the back side using reactive ion etching (RIE) and forming an exposed region, wherein the etching is selective to the bulk silicon;

using the epitaxial silicon as an endpoint indicator of the step of selectively etching; and accessing circuitry via the exposed region.

2. A method for analyzing a semiconductor device, according to claim 1, wherein the bulk silicon comprises highly doped silicon.

3. A method for analyzing a semiconductor device, according to claim 2, wherein the doping of the bulk silicon is higher than the doping of the epitaxial silicon.

4. A method for analyzing a semiconductor device, according to claim 1, wherein using the epitaxial silicon as an endpoint indicator of the step of selectively etching comprises:

monitoring an etch rate; and stopping the etching process, responsive to monitoring the etch rate.

5. A method for analyzing a semiconductor device, according to claim 4, wherein the etch rate of the bulk silicon is between about 10 to 20 times faster than the etch rate of the epitaxial silicon.

6. A method for analyzing a semiconductor device, according to claim 4, wherein the etching process is stopped when the etch rate slows to a threshold level defined as a function of the semiconductor device and the etching process.

7. A method for analyzing a semiconductor device, according to claim 6, wherein stopping the etching process responsive to monitoring the etch rate includes using a computer arrangement.

8. A method for analyzing a semiconductor device, according to claim 7, wherein the computer arrangement is adapted to control the RIE process.

9. A method for analyzing a semiconductor device, according to claim 1, wherein selectively etching the target region in the back side comprises:

generating a plasma and creating an etch gas;

reacting the etch gas with substrate in the back side; and removing byproduct gas produced by the reaction.

10. A method for analyzing a semiconductor device, according to claim 1, wherein directing an ion gas and etching the back side are carried out in a processing chamber.

11. A method for analyzing a semiconductor device, according to claim 10, wherein the processing chamber is at a vacuum of about 250 mtorr.

12. A method for analyzing a semiconductor device, according to claim 1, wherein directing ion gas comprises directing $SF_6$ and $N_2$ gas at about 48 SCCM.

13. A method for analyzing a semiconductor device, according to claim 1, further comprising sputtering substrate in the back side of the device.

14. A method for analyzing a semiconductor device, according to claim 1, wherein etching the target region includes etching with a temperature being monitored.

15. A method for analyzing a semiconductor device, according to claim 1, further comprising thinning the back side of the device to about 100 microns prior to selectively etching the target region using the ion gas.

16. A method for analyzing a semiconductor device, according to claim 1, wherein selectively etching the target region in the back side using reactive ion etching (RIE) includes etching at a range of substrate removal rates including a rate of about 4 micrometers per minute.

17. A method for analyzing a semiconductor device, according to claim 1, wherein etching the target region in the back side using reactive ion etching (RIE) includes forming a substantially planar and substantially non-pitted surface, the method further comprising imaging circuitry in the semiconductor device via the etched target region.

18. A method for analyzing a semiconductor device having a back side and a circuit side opposite the back side, wherein the semiconductor device includes bulk silicon in the back side and also includes epitaxial silicon, the method comprising:

globally thinning the back side of the device to a remaining substrate thickness of about 100 microns;

positioning the semiconductor device in a processing chamber;

drawing a vacuum of about 250 mtorr in the processing chamber;

monitoring temperature in the processing chamber;

directing $SF_6$ and $N_2$ at a target region in the back side;

using a power supply at about 500 watts, generating a plasma in the chamber and forming an etch gas;

reacting the etch gas with substrate in the back side and selectively etching bulk silicon in the target region in the back side and forming an exposed region, wherein the bulk silicon is more heavily doped than the epitaxial silicon, and wherein the etching is selective to the bulk silicon;

removing byproduct gas produced by the reaction;

monitoring the etch rate and detecting a slowing of the etch rate; and responsive to detecting a slowing of the etch rate, stopping the etch process.

* * * * *

UNITED STATES PATENT AND TRADEMARK OFFICE
CERTIFICATE OF CORRECTION

PATENT NO.    : 6,355,564 B1
DATED         : March 12, 2002
INVENTOR(S)   : Birdsley et al.

It is certified that error appears in the above-identified patent and that said Letters Patent is hereby corrected as shown below:

<u>Column 4,</u>
Line 16, both instances of "SCFM" should read -- SCCM --.

Signed and Sealed this

Second Day of July, 2002

Attest:

Attesting Officer

JAMES E. ROGAN
Director of the United States Patent and Trademark Office